US007051672B2

(12) United States Patent
Wright (10) Patent No.: US 7,051,672 B2
(45) Date of Patent: May 30, 2006

(54) SYSTEM FOR PROVIDING BENEFICIAL INSECTS OR MITES

(75) Inventor: Irvine W. Wright, Essex (GB)

(73) Assignee: Syngenta Participations AG, Basel (CH)

( * ) Notice: Subject to any disclaimer, the term of this patent is extended or adjusted under 35 U.S.C. 154(b) by 28 days.

(21) Appl. No.: 10/901,545

(22) Filed: Jul. 29, 2004

(65) Prior Publication Data
US 2005/0178337 A1    Aug. 18, 2005

Related U.S. Application Data

(60) Provisional application No. 60/546,589, filed on Feb. 20, 2004.

(30) Foreign Application Priority Data
Feb. 17, 2004 (GB) .................. 0403486.4

(51) Int. Cl.
*B65D 30/10*    (2006.01)
*B65D 33/36*    (2006.01)

(52) U.S. Cl. .............................. 119/6.5; 383/38; 383/41

(58) Field of Classification Search .............. 119/6.5; 383/38, 41; 449/27, 28; 47/31, 31.1
See application file for complete search history.

(56) References Cited

U.S. PATENT DOCUMENTS

| 2,813,602 | A | * | 11/1957 | MacArthur, Jr. ............. 224/220 |
| 4,498,420 | A | * | 2/1985 | Botterman et al. .......... 119/6.5 |
| 4,646,683 | A | * | 3/1987 | Maedgen, Jr. ................ 119/6.5 |
| 5,024,536 | A | * | 6/1991 | Hill .............................. 383/38 |
| 5,332,185 | A | * | 7/1994 | Walker, III ............... 248/346.2 |
| 6,125,145 | A | * | 9/2000 | Koyanagi et al. ....... 375/240.16 |

FOREIGN PATENT DOCUMENTS

| CH | 672874 A5 * | 1/1990 |
| GB | 2211717 A * | 7/1989 |

* cited by examiner

*Primary Examiner*—Michael Carone
*Assistant Examiner*—Bret Hayes
(74) *Attorney, Agent, or Firm*—Jenkins, Wilson, Taylor & Hunt, P.A.

(57) ABSTRACT

An apparatus for providing beneficial insects or mites to a cropping environment for application to the control of *thrips*, and methods for using the same is disclosed. The apparatus comprises first and second members joined by a hinge section, which also functions as a hook. At least one of the first and second members comprises a compartment and at least one emergence hole providing a passage between the compartment and the environment. The compartment comprises a formulation therein comprising beneficial insects or mites useful for controlling *thrips*. The apparatus is oriented when in use to have an inverted V- or U-type conformation, which creates a sheltered region around the emergence hole, protecting it from the environment.

68 Claims, 4 Drawing Sheets

SYSTEM FOR PROVIDING BENEFICIAL INSECTS OR MITES

RELATED APPLICATIONS

This application claims the benefit of priority under 35 U.S.C. § 119(a) of United Kingdom Patent Application No. GB 0403486.4, filed Feb. 17, 2004 and also claims the benefit of priority under 35 U.S.C. § 119(e) of U.S. Provisional Patent Application Ser. No. 60/546,589, filed Feb. 20, 2004; the disclosures of both of which are incorporated herein by reference in their entireties.

TECHNICAL FIELD

The presently disclosed subject matter relates to the field of insect and mite control. Specifically, it relates to the use of an apparatus for providing beneficial insects or mites for the control of phytophagous insect and mite pests, as well as methods for using the same.

BACKGROUND ART

Plant pests are a major factor in the loss of the world's important agricultural crops. About $8 billion is lost every year in the U.S. due to infestations of plants by non-mammalian pests including insects. In addition to losses in field crops, insect pests are also a burden to vegetable and fruit growers, to producers of ornamental flowers, and to home gardeners. For example, pest *thrips* such as *Frankliniella occidentalis* and *Thrips tabaci* cause extensive damage to horticultural crops such as salad vegetables, cut flowers and ornamental plants, resulting in significant economic loss to the growers.

Insect pests are mainly controlled by intensive applications of chemical pesticides, which are active through inhibition of insect growth, prevention of insect feeding or reproduction, or cause death. Although the use of such chemicals can result in good control of insect pests, the widespread use of chemical pesticides can result in the appearance of resistant insect varieties. Further, high levels of chemicals on horticultural crops, in particular salad vegetables, are undesirable to many consumers.

Therefore, an alternative method of pest control involving the use of beneficial insects or mites has been developed. The beneficial insects or mites are predatory towards pest insects such as *thrips*, and can be applied to crops to control insect pests. Beneficial insects or mites can be provided to crop plants in a variety of ways, for example manually or through a controlled release device. The use of beneficial insects or mites forms part of integrated crop management and integrated pest management programs, combining cultural, biological and chemical means to achieve sustainable pest control.

One example of a beneficial insect or mite system is the use of *Amblyseius cucumeris* as a predatory mite for the control of pest *thrips*. Existing systems involve the mite being provided either loose in bran and vermiculite for sprinkling onto crops, or in sachets for longer periods of protection. *Amblyseius cucumeris* feed on first instar *thrips* larvae, and control relies on complete cover of a crop with the predator before *thrips* establish. Repeated sprinkling of the predator over crops is labor intensive, wasteful and messy as much of the bran falls on the floor or gets stuck on the leaves. Establishment on crops is relatively slow, and therefore the existing sachet products were designed as an improved method of release.

The existing sachet products provide a continuous release of *Amblyseius cucumeris* for several weeks by maintaining a breeding population of the mite with a food source in the form of a grain mite (*Tyrophagus* spp.). The mites are contained in a bran matrix, with or without vermiculite. The breeding colony is maintained in a sachet with a hook attached to the sachet for placement onto plants, or onto wires used to support the crop. Mites emerge from the sachet onto the crop through a small perforation in the sachet, the emergence hole or aperture.

Although an improvement over previous systems, there are still several problems with the existing sachet products. In some growing systems, water or nutrient solutions are provided to plants through overhead irrigation systems, usually mist or sprinkler systems. In other growing systems, crops are grown under shade netting and natural rainfall wets the crop. In existing sachets, water can enter the sachet such that the contents become wet, the mites then cease to breed, and the sachet life is therefore reduced considerably. For example, water enters the sachet through the emergence aperture. Also, water collects on the seals on the outside of the sachet and is drawn into the sachet through capillary action along paper fibers. Another problem with existing sachets is that the hook becomes wet, distorts, and allows the sachet to fall to the ground. Further problems with existing sachets include a variable rate of release of beneficial mites, and a low overall release rate. This is a particular problem in wet conditions.

Therefore, there is a long-felt need in the art for an improved system for the delivery of beneficial insects or mites to cropping environments. The presently disclosed subject matter describes a new system for providing beneficial insects or mites, which overcomes these problems.

BRIEF SUMMARY

The presently disclosed subject matter is an apparatus for providing beneficial insects or mites to a cropping environment for application to the control of *thrips*, and methods for using the same. The novel apparatus protects the formulation comprising the beneficial insects or mites contained therein from fluctuations in the outside environment, and in particular from excess moisture contacting the formulation.

The apparatus includes a first member and a second member joined by a hinge section. Each of the first and second members has an inner wall and an outer wall. The first and second members are oriented about the hinge section such that when the apparatus is in use, the inner walls are positioned in opposition to each other, thereby creating a region sheltered along at least a portion of the inner walls. The apparatus further includes a compartment formed in at least one of the first and second members, the compartment containing a formulation therein, which comprises beneficial insects or mites. An emergence aperture is provided in at least one of the inner walls of the members and is positioned in the sheltered region. The emergence aperture provides a passage to the beneficial insects or mites from the compartment to the cropping environment.

In some embodiments the apparatus is constructed of at least two strips of film material having approximately equal dimensions. The strips each have a long axis and a short axis and are bonded together at the edges of the strips. In such embodiments, at least one compartment is defined by the bonded edges and an additional bond positioned parallel to the short axis of the strips. The compartment contains a formulation therein comprising beneficial insects or mites. At least one emergence aperture is provided in at least one of the strips, wherein the emergence aperture is positioned to provide passage to the beneficial insects or mites from the compartment to the cropping environment. A hinge section is positioned approximately midway along and perpendicular to the long axis. The hinge section permits folding of the strips upon themselves such that the apparatus is provided with an inverted V- or U-type conformation, with the at least one emergence aperture located on the inside of the conformation. In this conformation, the hinge section can also form a hook from which to hang the apparatus.

In other embodiments, the apparatus is constructed from at least one strip of film material folded in half, the strip having a long axis and a short axis. The edges of the folded strip are bonded together. At least one compartment is defined by the bonded edges and an additional bond positioned paralleled to the short axis of the folded strip. The compartment contains a formulation therein comprising beneficial insects or mites. At least one emergence aperture is provided in one side of the folded strip. The emergence aperture is positioned to provide passage to the beneficial insects or mites from the compartment to the cropping environment. A hinge section positioned approximately midway along and perpendicular to the long axis is provided. The hinge section permits folding of the folded strip upon itself such that the apparatus is provided with an inverted V- or U-type conformation, wherein the at least one emergence aperture is located on the inside of the conformation. In this conformation, the hinge section can also act as a hook from which to hang the apparatus.

In some embodiments, the first and second members are comprised of a water resistant and air permeable film material. The film material can be selected from the group consisting of paper, thermoplastic material, polythene-coated paper, polythene-coated fabric, and porous PTFE. In some embodiments where the film material comprises polythene-coated paper, the polythene has a density of between about 5 and 100 g/m$^2$. In some embodiments where the film material is a paper, the paper is selected from the group consisting of machine glazed bleached kraft paper, grid-lacquer paper, and medical paper.

In some embodiments, the compartment is formed by bonding together the outer edges of the inner wall and the outer wall to form a seal. The seal can be a substantially seamless seal, thereby effectively preventing water from collecting on the seal.

In yet other embodiments, both of the first and second members each comprise a compartment. In such a configuration, the formulation can be distributed evenly between each of the compartments. Further, in such configurations, each compartment can comprise at least one emergence aperture.

In yet other embodiments, only one of the first and second members of the apparatus comprises a compartment. In some embodiments of this configuration, the member not comprising a compartment can weigh substantially the same as the other member comprising a compartment when the compartment includes therein the formulation. The member not comprising a compartment then acts as a counter balance to the member comprising the compartment.

In still other embodiments, the beneficial insects or mites are predator insects or mites. In some embodiments the predator insects or mites are *Amblyseius cucumeris, Frankliniella occidentalis*, or *Thrips tabaci*. The formulation can further comprise a food for the predator insect or mite. The food can be a viable grain or prey insects or mites. In embodiments where the predator food is a prey, the prey can be *Tyrophagus* spp., *Acarus siro*, or combinations thereof. In embodiments where the prey is *Tyrophagus* spp., the species can include *Tyrophagus putrescentiae, Tyrophagus tropicus*, or combinations thereof. In some embodiments the formulation further comprises a prey food to sustain the prey. The prey food can be in some embodiments steamed bran or a 3:1 ratio of yeast and wheat germ. In some embodiments the formulation comprises *Amblyseius cucumeris* and *Tyrophagus putrescentiae* in a ratio of approximately 1:10.

In still other embodiments of the apparatus, the at least one emergence hole is positioned in a region of the inner walls proximate to the hinge section. In some embodiments the emergence hole has a diameter of between about 0.5 mm and about 5.0 mm.

In some embodiments the cropping environment is a sheltered cropping environment.

The presently disclosed subject matter also includes methods of using the apparatus. Disclosed herein are methods for providing a steady release rate of beneficial insects or mites. In some embodiments, the method comprises first providing beneficial insects or mites in the apparatus of the presently disclosed subject matter and then releasing the beneficial insects or mites at a steady rate. The steady rate release in some embodiments means releasing the beneficial insects or mites at a generally constant rate over about a six week period.

Also provided herein are methods of controlling *thrips* in a cropping environment. In some embodiments, the method comprises first providing beneficial insects or mites in the apparatus of the presently disclosed subject matter; then releasing the beneficial insects or mites from the apparatus into the cropping environment; and finally controlling the *thrips* in the cropping environment.

Some of the objects of the subject matter disclosed herein having been stated hereinabove, and which are addressed in whole or in part by the presently disclosed subject matter, other objects will become evident as the description proceeds when taken in connection with the accompanying drawings as best described hereinbelow.

DETAILED DESCRIPTION

Figure 1:
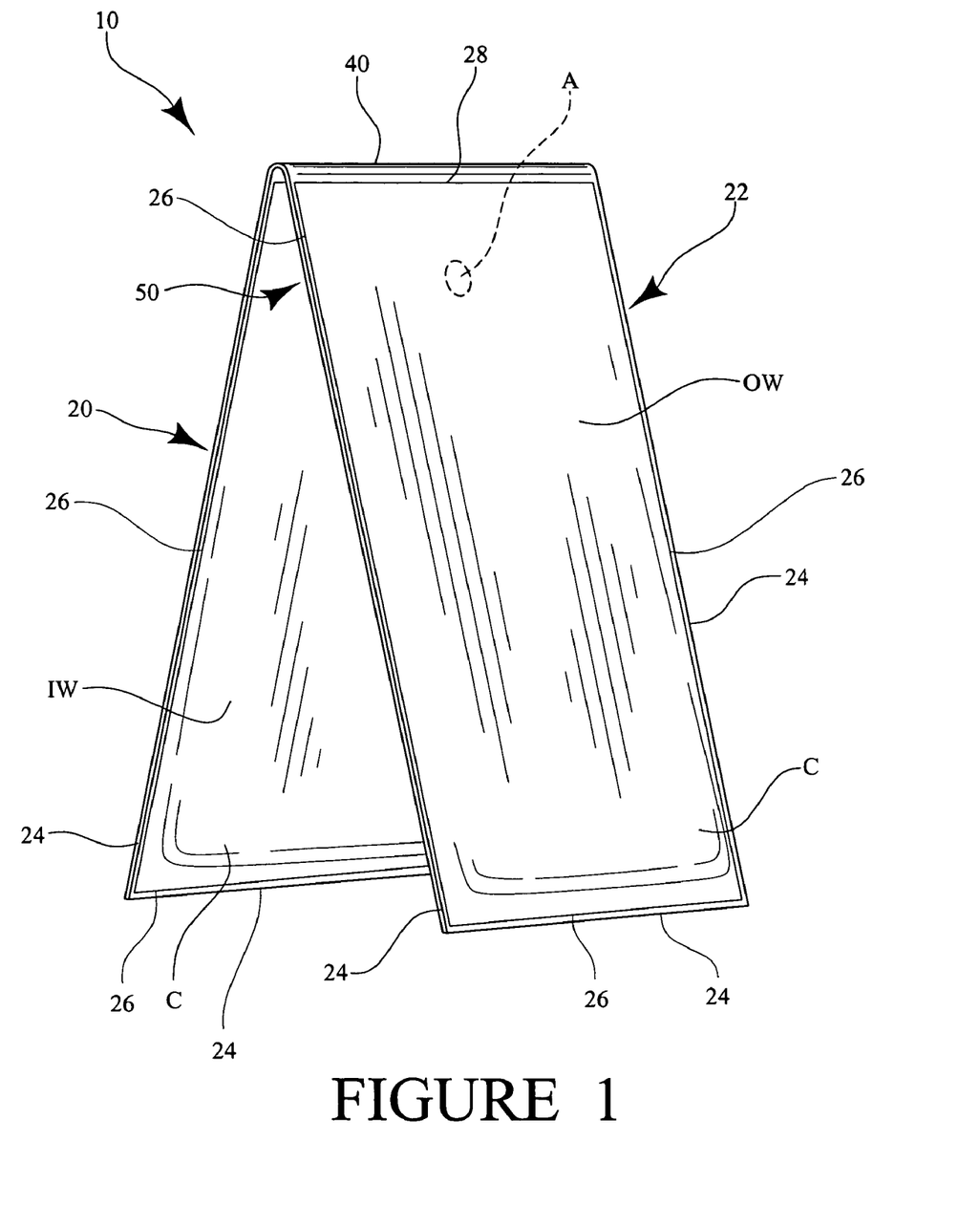
FIG. 1 is a perspective view of the novel apparatus disclosed herein shown folded for use in its inverted V- or U-type conformation.
Figure 5:
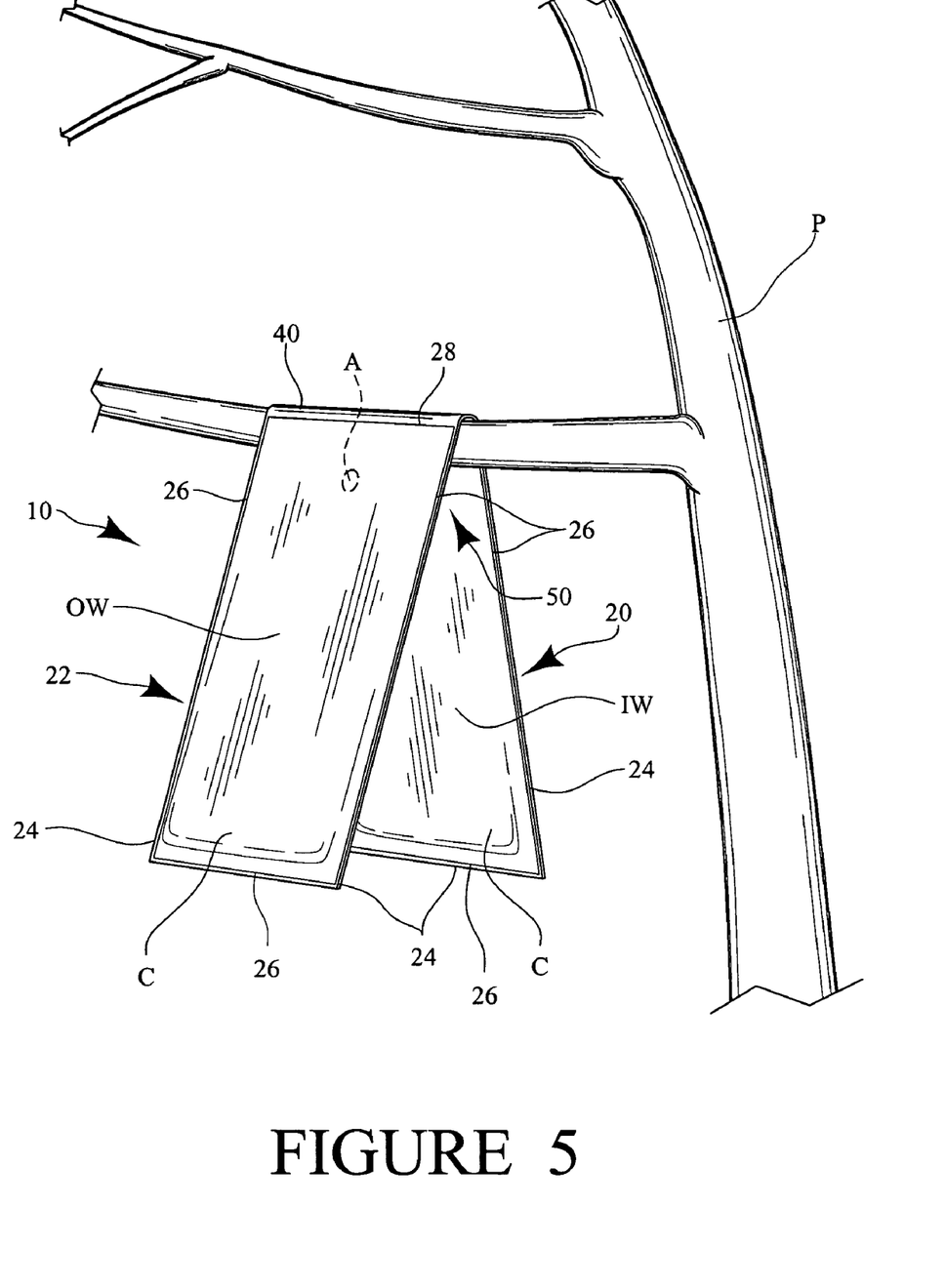
FIG. 5 is a perspective view of the novel apparatus disclosed herein shown in use by being inverted and suspended on a plant with the hinge section acting as a hook.

Referring now to FIGS. 1–5, an apparatus 10 for providing beneficial insects or mites to a cropping environment is disclosed and can best be seen in FIGS. 1 and 5. Apparatus 10 functions to permit steady release of beneficial insects or mites from apparatus 10 over an extended period of time. Apparatus 10 is able to provide a steady release rate of beneficial insects or mites over an extended period of time due in part to its novel configuration, which shields the interior of apparatus 10 containing the beneficial insects or mites from fluctuations in the environment, including in particular increased humidity and temperature fluctuations.

The cropping environments in which apparatus 10 can be used include, but are not limited to, protected cropping environments. The term 'protected cropping environment' refers to a variety of growing situations, including for example growing crops in greenhouses, plastic tunnels, glasshouses, shade-houses and other similar environments. However, the presently disclosed subject matter is not limited to use in such environments, but can alternatively be used outdoors, for example in a field.

As shown in FIG. 1, apparatus 10 comprises a first region or member 20 and a second region or member 22 joined together by a fold or hinge section 40. First and second members 20 and 22 each have an inner wall IW and an outer wall OW. Inner and outer walls IW and OW are joined at each of outer edges 24 by edge seals 26.

Edge seals 26 can be formed using any of various sealing methods generally known in the art, including but not limited to sealing using glue, heat, tape, or fixing together by any other means. In some embodiments, edge seals 26 are formed by heating polythene-coated paper.

In some embodiments, edge seals 26 can measure approximately 5 to 10 mm in width. Preferably, edge seals 26 are seamless, as this provides the advantage of discouraging water accumulation along edge seals 26, which in turn helps prevent wicking of the water into the interior of apparatus 10 over time. Prior art 'sachet' products have serrated seals which provide a series of ridges along the edges of the sachet. Further, the process of making a serrated seal often causes the edges of the product to curl. The presence of these ridges and curls allows water to collect on the outside of the sachet, and in time, the water wicks along paper fibers and the sachet contents become wet. This disrupts the microenvironment within the sachet, and therefore can considerably shorten the life of the system.

In one preferred embodiment of the presently disclosed subject matter, the substantially seamless seal is a flat seal. The subject matter disclosed herein also includes other types of seals which do not result in ridges, pockets or dips in which water could accumulate.

Figure 2:
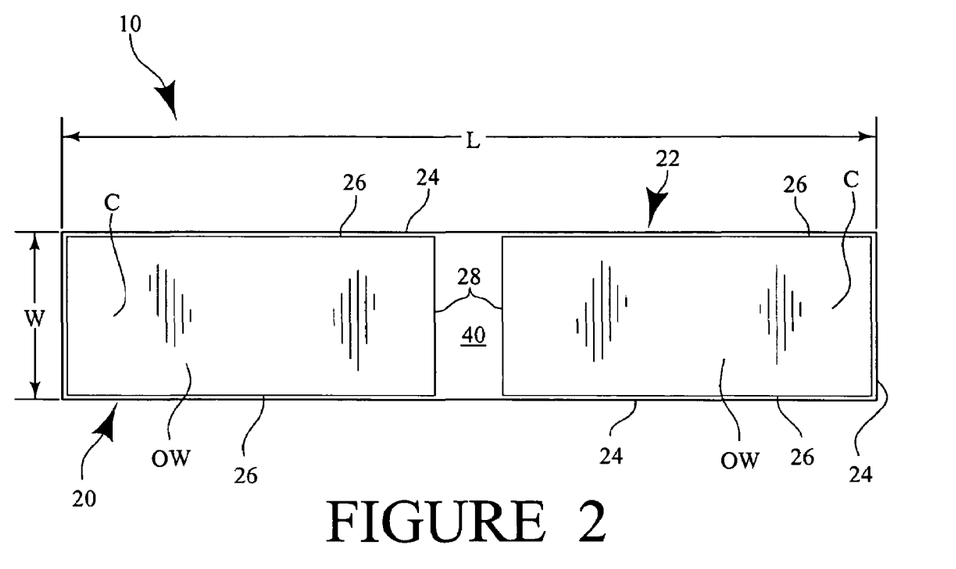
FIG. 2 is a top plan view of the novel apparatus disclosed herein shown in its unfolded configuration.
Figure 3:
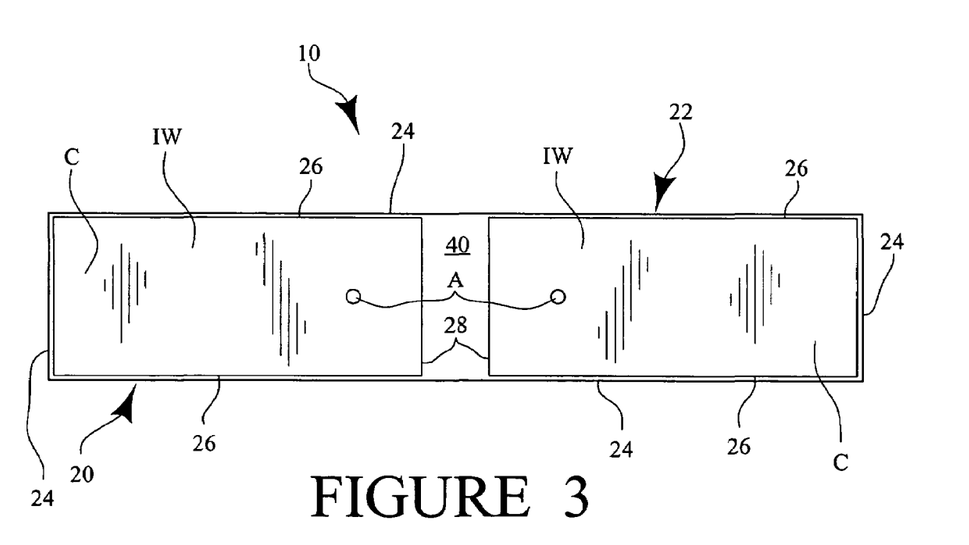
FIG. 3 is a bottom plan view of the novel apparatus disclosed herein shown in its unfolded configuration.
Figure 4:
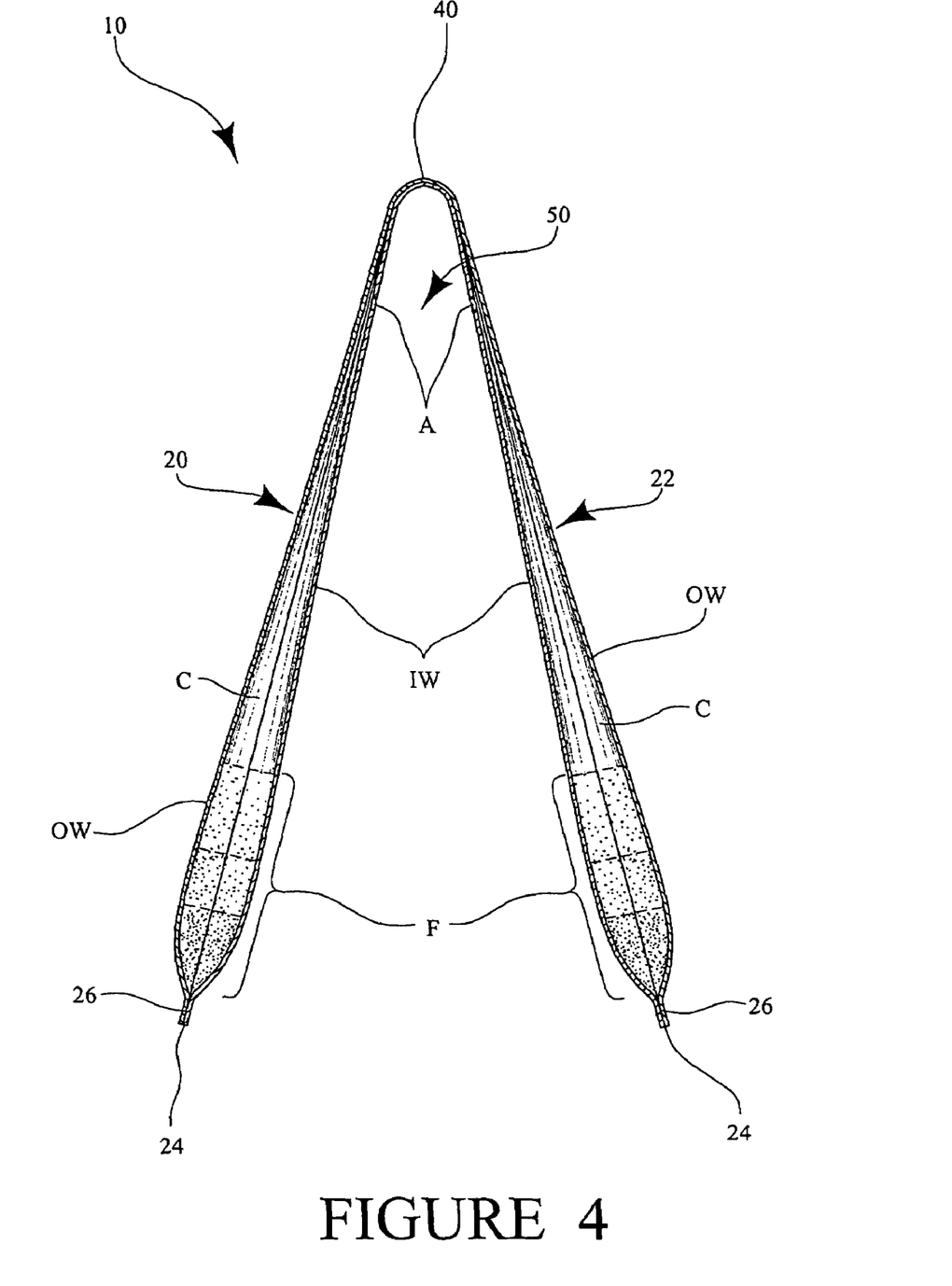
FIG. 4 is a vertical cross-sectional view of the novel apparatus disclosed herein showing the formulation contained therein.

As best shown in FIGS. 2 and 3, seamless edge seals 26 bond outer edges 24 of inner and outer walls IW and OW to define a compartment C in one or both of first and second members 20 and 22. An additional bond 28 can be included to further define compartment C and seal it from the outside environment. In other embodiments of the presently disclosed subject matter, apparatus 10 includes compartment C in only one of first and second members 20 and 22. In some of these embodiments, the non-compartment member is a substantially planar sheet. In embodiments where apparatus 10 includes compartment C in only one of first and second members 20 and 22, member 20 or 22 not having compartment C formed therein, can have a weight substantially the same as member 20 or 22 comprising compartment C when compartment C includes a formulation F comprising the beneficial insects or mites. In this configuration, member 20 or 22 without compartment C acts as a counterbalance to the other member 20 or 22, thereby facilitating proper positioning of apparatus 10 when in use.

In embodiments where both first and second members 20 and 22 comprise compartment C, formulation F can be distributed evenly between the two compartments C in order to balance first and second members 20 and 22. Alternatively, formulation F can be included in only one of the two compartments C, and the opposite compartment C can contain a ballast to counter the weight of the compartment C comprising beneficial insects or mites. Alternatively, the two compartments C can comprise formulations F, each of which comprises different beneficial insects or mites. In some embodiments, one of the two compartments C is empty.

As best shown in FIG. 3, apparatus 10 further includes at least one emergence hole or aperture A positioned in inner walls IW of first and second members 20 and 22. Preferably, emergence aperture A is found only in first or second members 20 and 22, which include compartment C. In some embodiments, apparatus 10 comprises multiple emergence apertures A, located either in one or both of first and second members 20 and 22.

Emergence aperture A provides passage to the beneficial insects or mites in formulation F from compartment C to the cropping environment. Emergence aperture A is positioned in inner walls IW so that when apparatus 10 is in its folded conformation for use, water cannot enter emergence aperture A due to the 'umbrella' effect of the inverted V- or U-type folded conformation (see FIG. 1). In one aspect of the presently disclosed subject matter, emergence apertures A are located in the top half of inner walls IW when apparatus 10 is in its inverted V- or U-type conformation. In a further aspect of the presently disclosed subject matter, each emergence aperture A is between approximately 0.5 mm and 5 mm in diameter. In some embodiments, emergence apertures A are each approximately 1 mm in diameter. In other embodiments, emergence apertures A are each approximately 2 mm in diameter. In other embodiments, emergence apertures A are each approximately 3 mm in diameter.

Inner and outer walls IW and OW are comprised of film material. Preferably, the film material is water resistant to prevent moisture from entering compartment C, which can be a factor in reducing the number of beneficial insects and mites emerging from apparatus 10 over an extended time period. In some embodiments of the presently disclosed subject matter, the film material is not only water resistant, but also gas permeable. This both protects the beneficial insects and mites from moisture, while also allowing the free exchange of air into and out of compartment C needed for the beneficial insects or mites to thrive. As such, the term 'film material' as used herein includes any material which is preferably water resistant and air permeable.

In one aspect of the presently disclosed subject matter, useful films include paper, thermoplastics (such as polythene) and polythene-coated paper. Further examples of other suitable materials, include fabric coated with polythene, and porous polytetrafluoroethylene (PTFE), for example GORE-TEX®. In embodiments where the film material is paper, suitable paper types include, for example, machine glazed bleached kraft paper, grid lacquer paper or medical paper. The paper density can be between about 10 and 100 $g/m^2$. As non-limiting examples, for bleached kraft paper, the density can be approximately 40 $g/m^2$, and for grid lacquer paper, the density can be approximately 60 $g/m^2$.

In particular embodiments, the film material is polythene-coated paper with a density of between about 5 and 100 $g/m^2$. In another aspect of the presently disclosed subject matter, the polythene density is between about 10 and 75 $g/m^2$. In a further aspect of the presently disclosed subject matter, the polythene density is between about 15 and 50 $g/m^2$. In yet another aspect of the presently disclosed subject matter, the polythene density is approximately 20 $g/m^2$.

The water resistant property of the film material refers to an ability of the film material to either repel or not absorb water. It includes, but is not limited to materials which are totally impervious to water (waterproof). Therefore, water applied to or falling on the system will run off, rather than be absorbed into the film material. The film material is preferably lightweight so that the system can easily be hung from branches of plants without damaging them.

FIG. 5 shows apparatus 10 in use. Apparatus 10 can be stored unfolded as shown in FIGS. 2 and 3, which can be convenient for packaging and distributing the product. However, when in use, apparatus 10 is folded with first and second members 20 and 22 oriented about hinge section 40 such that inner walls IW are positioned in opposition to each other and apparatus 10 has an inverted V- or U-shaped conformation. This conformation creates a region 50 sheltered from the environment along at least a portion of inner walls IW, as shown in FIGS. 1 and 5.

Hinge section 40 can be positioned anywhere along apparatus 10. In the embodiment shown in the figures, hinge section 40 is positioned approximately centrally at a point along lengthwise axis L.

The presently disclosed subject matter is not limited to strict inverted V- or U-conformations, but includes systems which are capable of being folded into similar shapes, or an intermediate shape between V- and U-shaped. In one aspect of the presently disclosed subject matter, the inverted V- or U-type conformation is present at or around the position of hinge section 40 itself. Outer edges 24 can optionally comprise further folds so that the overall configuration of apparatus 10 does not closely resemble an inverted V- or U-type conformation.

In some embodiments of the subject matter disclosed herein, first and second members 20 and 22 on either side of hinge section 40 are different lengths or sizes. In other embodiments, first and second members 20 and 22 on either side of hinge section 40 are substantially similar in size. The subject matter disclosed herein further includes first and second members 20 and 22 which are constructed individually, and subsequently sealed together at hinge section 40 so that they can be folded into an inverted V or U-type conformation.

In another embodiment of the presently disclosed subject matter, there are an equal number of members 20 and 22 either side of the fold. However, the presently disclosed subject matter is not limited to a single member 20 or 22 on either side of hinge section 40, but encompasses apparatuses 10 comprising multiple members 20 and 22 on each side of hinge section 40.

Sheltered region 50 provides a stable microclimate or microenvironment, effectively sheltering emergence apertures A from environmental variations such as temperature and humidity, resulting in a steady release rate of beneficial insects or mites over approximately a six week period. In particular, sheltered region 50 protects emergence apertures A from moisture resulting from, for example, rain and irrigation systems, thereby keeping humidity levels even. Therefore, when apparatus 10 is folded into a V- or U-shaped conformation, sheltered region 50 prevents excess moisture from entering emergence apertures A, thereby protecting formulation F from moisture damage. Alternatively, in some embodiments, hinge section 40 can be positioned asymmetrically along apparatus 10 such that when folded a different conformation ensues. However, it is often most beneficial to provide protection from at least two directions, as in the inverted V- or U-shaped conformation shown in the figures, to better preserve the microenvironment from fluctuations in temperature (due to, for example, time of day or positioning relative to the sun) and humidity (due to, for example, rain or other irrigation falling at an angle other than directly vertical onto apparatus 10).

The inverted V- or U-shaped conformation of apparatus 10 further permits hinge section 40 to also function as a hook from which to hang apparatus 10. As shown in FIG. 5, apparatus 10 when in use can be freely suspended from hinge section 40 over a branch or stem from a plant P to be protected so that first and second members 20 and 22 are either side of the branch. Apparatus 10 is not limited to being suspended only from branches, but also can be suspended from any generally horizontal structure including cables, wires, string, etc., as will be easily appreciated by one of skill in the art. Alternatively, apparatus 10 can be freestanding, for example on the ground or pot in which the plant P is growing.

Optionally, apparatus 10 can comprise a hook, for example made from plastic. Such a further hook can be located at or near hinge section 40 and can, for example be used to hang apparatus 10 from branches where the leaves are close together so that hooking using hinge section 40 is difficult. Preferably however, apparatus 10 is less than 5 cm in width so that it can easily be hooked over the branches of plant P between leaf nodes.

In one aspect of the presently disclosed subject matter, apparatus 10 measures approximately 20 cm in length as measured along axis L and approximately 4.5 cm in width as measured along short axis or width W. If apparatus 10 is folded in half with hinge section 40 midway along axis L, each of first and second members 20 and 22 measures approximately 10 cm by approximately 4.5 cm. When in its folded conformation, hinge section 40 itself can, for example, measure between about 1 and 10 mm in width to accommodate branches and wires of different thickness.

With apparatus 10 suspended by hinge section 40 on plant P, the beneficial insects or mites within formulation F can leave compartment C at a steady release rate and enter the environment through emergence aperture A. The beneficial insects or mites can then gain easy access to plant P through the contact of hinge section 40 with plant P and thereby redistribute across plant P and other plants in proximity to plant P in order to control pest insects or mites by predation.

Apparatus 10 can be constructed using any of the commonly known manufacturing processes practiced in the art. As a non-limiting example, in some embodiments apparatus 10 is constructed from at least two strips of the film material of approximately the same size, each having a long axis L and a short axis W (see FIG. 2). One strip of the film material is overlaid on the other, bonded or sealed together at outer edges 24 to form seamless edge seals 26 and further sealed together at least once at a point along long axis L and parallel to short axis W to form first and second members 20 and 22, which are substantially planar regions. At least one of which regions comprises compartment C defined by additional bond 28 and seamless edge seals 26, wherein compartment C comprises formulation F containing beneficial insects or mites.

In an alternative manufacturing process, apparatus 10 can be constructed from at least one strip of the film material, folded along one edge 24, sealed together at the remaining outer edges 24, and further sealed or bonded at least once at a point along long axis L and parallel to short axis W to form first and second members 20 and 22, which are substantially planar regions. At least one of which regions comprises compartment C defined by additional bond 28 and seamless edge seals 26, wherein compartment C comprises formulation F containing beneficial insects or mites.

The presently disclosed subject matter includes strips of the film material which are any shape or size. Typically, the strip of the film material will be rectangular, for example measuring approximately 20 cm by 4.5 cm.

Regardless of the manufacturing process, after construction and as previously discussed apparatus 10 can be packaged and shipped unfolded for convenience, and is capable of then being folded by the user to form an inverted V- or U-type conformation wherein emergence aperture or apertures A are located on the inside of the folded conformation, that is on inner walls IW, so that water cannot enter compartment C through emergence aperture or apertures A. Alternatively, apparatus 10 can be folded into the V- or U-shaped conformation prior to packaging.

As used herein, the phrase 'release rate' refers to the number of beneficial insects or mites that are released or emerge from compartment C over a period of time. A steady release rate refers to the release rate being approximately constant over approximately a six week period commencing when apparatus 10 is put in use. For example, the release rate can be between approximately 200 and 300 insects or mites released each week. Therefore a total of approximately 1500 insects or mites can be released over approximately a six week period. A high release rate can be in the order of 700 insects or mites per week while a low release rate can be 50 insects or mites per week. Prior art products typically have a release rate which is not steady, but fluctuates over time, for example ranging from 100 mites per week to 750 mites per week.

Emergence of prey mites can be damaging to the crop plants. Therefore an important feature of the subject matter disclosed herein is formulation F within compartment C. It is important to achieve the correct initial balance between predator and prey to ensure a plentiful and uniform emergence of *Amblyseius cucumeris* (predator) without excessive emergence of *Tyrophagus putrescentiae* (prey food for predator). Due to the conformation of apparatus 10, the rate of escape of prey mites is significantly reduced, therefore resulting in decreased damage to crop plants. For example, typically greater than 10,000, and often greater than 20,000 *Tyrophagus* spp. escape from prior art products over a 6 week period, while fewer than 10,000 *Tyrophagus* spp. escape from the presently disclosed system over the same time period.

In one embodiment of the subject matter disclosed herein, there is provided a system suitable for providing beneficial insects or mites in a protected cropping environment, wherein the beneficial insects or mites are maintained as a breeding population. In one aspect, compartment C comprises a food source for the beneficial insects or mites. In a further aspect, the food source consists of prey insects or mites. In yet a further aspect, compartment C further comprises a food source for the prey insects or mites.

In some embodiments of the presently disclosed subject matter, at least one compartment C contains a formulation F comprising viable *Amblyseius cucumeris*, a predatory mite which can be used for the control of *thrips* such as *Frankliniella occidentalis*, and *Thrips tabaci*; viable grain or stored product pest mites; and bran. The grain or stored product pest mites can, for example be *Tyrophagus* species such as *Tyrophagus putrescentiae*, *Tyrophagus tropicus*, or another species such as *Acarus siro*. Alternatively, the grain or stored product pest mites can be a mixture of these two species. In one aspect of the presently disclosed subject matter, the grain or stored product pest mites are *Tyrophagus putrescentiae*. In some embodiments, the *Amblyseius cucumeris* and grain or stored product pest mites are present in a ratio of approximately 1:10. This ratio of predatory mites to prey mites is important for maintaining a successful breeding population over a period of six weeks or longer. If too few prey mites are present in the system, they will be eaten quickly by the predatory mites, resulting in a high number of predatory mites being released over a short time period, and the system having a short life. In contrast, if too many prey mites are present in formulation F, they may escape through emergence hole A. This is undesirable since prey mites can cause damage to crop plants. Therefore, formulation F is a key aspect of the present system for effective pest control.

In one aspect of the presently disclosed subject matter, at least one compartment C comprises a formulation F consisting of one *Amblyseius cucumeris* for every 10 *Tyrophagus putrescentiae* and 0.52 g of prey food mix. The prey food mix can be made with steamed bran and a 3:1 mix of yeast and wheat germ. In some embodiments, the formulation F is split equally between two or more compartments C.

The presently disclosed subject matter also includes other types of beneficial insects and mites, which are capable of being maintained as a breeding colony. In particular, the presently disclosed subject matter includes other species of *Amblyseius*. Further, the subject matter disclosed herein is not limited to the use of *Tyrophagus putrescentiae* as a food source, but includes other species of *Tyrophagus*, such as *Tyrophagus tropicus*, other mites such as *Acarus siro*, or any other insect or mite which the beneficial insect or mite could feed on. The presently disclosed subject matter further includes the use of an alternative food source to grain mites. This is useful to reduce damage to crop plants caused by grain or stored product pest mites that escape from the system.

In some embodiments of the presently disclosed subject matter, there is provided a method for providing a steady release rate of beneficial insects or mites comprising providing the beneficial insects or mites in apparatus 10 described above and releasing the beneficial insects or mites at a steady rate.

Also provided herein are methods of controlling *thrips* in a cropping environment. In some embodiments, the method comprises first providing beneficial insects or mites in apparatus 10; then releasing the beneficial insects or mites from apparatus 10 into the cropping environment; and finally controlling the *thrips* in the cropping environment.

The methods and apparatus described above can be used to control, for example, Western Flower *Thrips, Frankliniella occidentalis*. However, the methods and apparatus are also suitable for the control of other *thrip* species, such as *Thrips tabaci*, in addition to other pest insects.

The methods and apparatus described above can be used for the control of pest insects on horticultural crops in a cropping environment. Horticultural crops for which the subject matter disclosed herein can be used include, for example, salad vegetables, cut flowers and ornamental plants.

EXAMPLES

The presently disclosed subject matter will be further described by reference to the following detailed examples. The examples are provided for the purposes of illustration only, and are not intended to be limiting unless otherwise specified.

Example 1

A. Aims

A trial was established to compare emergence of *Amblyseius cucumeris* and a prey mite (*Tyrophagus putrescentiae*) from the presently disclosed novel system compared to the standard controlled release system sachets produced by Syngenta Bioline, as well as the products of two competitors.

B. Trial Design

Several different products were tested in the trial. Table 1 below indicates these products.

TABLE 1

| Product | Description |
| --- | --- |
| A | Novel system 1: 40 g/m² paper coated with 20 g/m² polyethylene |
| B | Novel system 2: 40 g/m² paper coated with 50 g/m² polyethylene |
| C | AMBLYLINE CU CRS ™, Syngenta Bioline, Essex, England |
| D | AMBLYSEIUS-BREEDING-SYSTEM (ABS) ™, Biobest N.V., Westerlo, Belgium |
| E | THRIPEX-PLUS ™, Koppert BV, Rotterdam, Netherlands |

All product types were suspended over plants in a greenhouse in identical conditions, with overhead watering from an automatic sprinkler system once each day to represent the watering systems used in many ornamental crops.

Existing sachet systems were fitted with waterproof plastic hooks to ensure that they remained hanging where placed for the duration of the trial, therefore artificially prolonging the life of existing sachets which usually fall to the ground within two weeks, after the hooks collapse. This was necessary to compare the effects of watering on the contents of the different systems.

C. Assessments

Due to the practical difficulties in measuring mite emergence under overhead irrigation, several sachets/systems of each of products A–E were removed from the test conditions at seven day intervals, taken to an environment room, and suspended over a sticky surface to trap mites which emerged over the following 7 days. The numbers of predator mites (*Amblyseius*) and prey mites (*Tyrophagus*) were counted.

D. Results

The cumulative number of *Amblyseius* which emerged during the trial are shown in Table 2 below.

TABLE 2

| Product | Week 1 | Week 2 | Week 3 | Week 4 | Week 5 | Week 6 |
| --- | --- | --- | --- | --- | --- | --- |
| A | 202 | 746 | 1014 | 1303 | 1456 | 1490 |
| B | 216 | 754 | 1009 | 1371 | 1486 | 1531 |
| C | 242 | 525 | 648 | 885 | 892 | 1168 |
| D | 23 | 109 | 112 | 373 | 648 | 664 |
| E | 225 | 422 | 654 | 991 | 1757 | 2059 |

The cumulative number of *Tyrophagus* which emerged during the trial are shown in Table 3 below.

TABLE 3

| Product | Week 1 | Week 2 | Week 3 | Week 4 | Week 5 | Week 6 |
| --- | --- | --- | --- | --- | --- | --- |
| A | 1790 | 4214 | 5245 | 8216 | 8364 | 8392 |
| B | 2871 | 4566 | 5704 | 7148 | 7258 | 7301 |
| C | 3982 | 5793 | 13200 | 16345 | 19999 | 20664 |
| D | 3343 | 9569 | 10642 | 13791 | 14054 | 14624 |
| E | 1273 | 8934 | 23922 | 36290 | 44351 | 47382 |

E. Summary

There is no significant difference between novel products A and B.

Emergence of *Amblyseius cucumeris* is higher throughout most of the release period from the novel systems (A and B) than from product C.

Emergence of *Amblyseius cucumeris* from the novel systems (A and B) is significantly higher throughout the release period than for product D.

Emergence of *Amblyseius cucumeris* is more uniform throughout the release period than that of product E.

Emergence of *Tyrophagus putrescentiae* from the novel systems (A and B) is lower than from product C.

Emergence of *Tyrophagus putrescentiae* from the novel systems (A and B) is lower than from either of products D and E.

Example 2

A. Aims

A trial was established to compare populations of *Amblyseius cucumeris* found on plants (chrysanthemum) to which the presently disclosed novel system and the standard controlled release system sachets produced by Syngenta Bioline had been attached.

B. Trial Design

Two different products were tested in the trial. Table 4 below indicates these products.

TABLE 4

| Product | Description |
| --- | --- |
| A | Novel system 1: 40 g/m² paper coated with 20 g/m² polyethylene |
| B | AMBLYLINE CU CRS ™, Syngenta Bioline, Essex, England |

Both product types were suspended from wire framework used to support the stems of flowers in a greenhouse in identical conditions, with overhead watering from an automatic sprinkler system as needed, typically for 15 minute intervals 1–3 times per week.

Product B sachet systems were fitted with waterproof plastic hooks to ensure that they remained hanging where placed for the duration of the trial, therefore artificially prolonging the life of existing sachets which usually fall to the ground within two weeks, after the hooks collapse. This was necessary to compare the effects of watering on the contents of the different systems.

C. Assessments

In order to measure mite numbers on plants, each week, for each treatment, three (3) batches of five (5) whole plants were pulled from the crop area at random, and bagged separately. The groups of plants were then immersed in ethyl alcohol to kill any mites or insects present, and washed through a sieve to collect these mites or insects. These washings were then examined and identified using a binocular microscope. The data presented represents the summed data from each treatment.

D. Results

The total number of *Amblyseius* from all the plants (15) which emerged during each tested time period of the trial are shown in Table 5 below.

TABLE 5

Total Number *Amblyseius* Found on 15 Plants

| Days After Introduction | Product A | Product B |
|---|---|---|
| 7 | 20 | 2 |
| 14 | 27 | 3 |
| 21 | 127 | 13 |
| 28 | 166 | 67 |
| 35 | 281 | 137 |
| 42 | 419 | 227 |

The average number of *Amblyseius* found on each plant which emerged during each tested time period of the trial are shown in Table 6 below.

TABLE 6

Average Number *Amblyseius* Found Per Plant

| Days After Introduction | Product A | Product B |
|---|---|---|
| 7 | 1.3 | 0.1 |
| 14 | 1.8 | 0.2 |
| 21 | 8.5 | 0.9 |
| 28 | 11.1 | 4.5 |
| 35 | 18.7 | 9.1 |
| 42 | 27.9 | 15.1 |

E. Summary

The novel product A is superior in performance to product B as emergence of *Amblyseius cucumeris* is higher throughout the release period from the novel system A than from product B.

Populations of *Amblyseius cucumeris* found on plants and originating from Product A remain high up to at least 42 days.

Example 3

A. Aims

A trial was established to compare populations of *Amblyseius cucumeris* found on plants (chrysanthemum) to which the presently disclosed novel system and a THRIPEX-PLUS™ sachet (Koppert BV, Rotterdam, Netherlands) had been attached.

B. Trial Design

Two different products were tested in the trial. Table 7 below indicates these products.

TABLE 7

| Product | Description |
|---|---|
| A | Novel system 1: 40 g/m$^2$ paper coated with 20 g/m$^2$ polyethylene |
| B | THRIPEX-PLUS ™ Koppert BV, Rotterdam, Netherlands |

Both product types were suspended from wire framework used to support the stems of flowers in a greenhouse in identical conditions, with overhead watering from an automatic sprinkler system as needed, typically for 15 minute intervals 1–3 times per week.

Product B sachet systems were used as commercially available without further modification.

C. Assessments

In order to measure mite numbers on plants, each week, for each treatment, three (3) batches of five (5) whole plants were pulled from the crop area at random, and bagged separately. The groups of plants were then immersed in ethyl alcohol to kill any mites or insects present, and washed through a sieve to collect these mites or insects. These washings were then examined and identified using a binocular microscope. The data presented represents the summed data from each treatment.

D. Results

The total number of *Amblyseius* from all the plants (15) which emerged during each tested time period of the trial are shown in Table 8 below.

TABLE 8

Total Number *Amblyseius* Found on 15 Plants

| Days After Introduction | Product A | Product B |
|---|---|---|
| 5 | 13 | 12 |
| 13 | 48 | 46 |
| 20 | 77 | 26 |
| 27 | 187 | 26 |
| 34 | 298 | 14 |

The average number of *Amblyseius* found on each plant which emerged during each tested time period of the trial are shown in Table 9 below.

TABLE 9

Average Number *Amblyseius* Found Per Plant

| Days After Introduction | Product A | Product B |
|---|---|---|
| 5 | 0.87 | 0.80 |
| 13 | 3.20 | 3.07 |
| 20 | 5.13 | 1.73 |
| 27 | 12.47 | 1.73 |
| 34 | 19.87 | 0.93 |

E. Summary

The novel product A is superior in performance to product B as emergence of *Amblyseius cucumeris* is higher throughout the release period from the novel system A than from product B.

Populations of *Amblyseius cucumeris* found on plants and originating from Product A remain high up to at least 34 days, whereas populations found on plants and originating from product B are declining by 34 days.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. An apparatus for providing beneficial insects or mites to a cropping environment, comprising:
   (a) a first member and a second member, each member having an inner wall and an outer wall;
   (b) a hinge section joining said first and second members, said first and second members oriented about said hinge section when said apparatus is in use such that said inner walls are positioned in opposition to each other, thereby creating a region sheltered along at least a portion of said inner walls;
   (c) a compartment formed in at least one of said first and second members, said compartment containing a formulation therein comprising beneficial insects or mites; and
   (d) at least one emergence aperture in at least one of said inner walls and positioned in said sheltered region, said emergence aperture providing passage to said beneficial insects or mites from said compartment to said cropping environment.

2. The apparatus of claim 1, wherein said first and second members are comprised of a water resistant and air permeable film material.

3. The apparatus of claim 2, wherein said film material is selected from the group consisting of paper, thermoplastic material, polythene-coated paper, polythene-coated fabric, and porous PTFE.

4. The apparatus of claim 3, wherein said film material comprises polythene-coated paper and the polythene has a density of between 5 and 100 $g/m^2$.

5. The apparatus of claim 3, wherein said film material is a paper selected from the group consisting of machine glazed bleached kraft paper, grid lacquer paper, and medical paper.

6. The apparatus of claim 1, wherein when said apparatus is in use and said first and second members are oriented about said hinge section such that said inner walls are positioned in opposition to each other, and said apparatus exhibits an inverted V- or U-shaped conformation.

7. The apparatus of claim 6, wherein said hinge section forms a hook from which to hang said apparatus.

8. The apparatus of claim 1, wherein said compartment is formed by bonding together the outer edges of said inner wall and said outer wall to form a seal.

9. The apparatus of claim 8, wherein said seal is a substantially seamless seal effectively preventing water from collecting on said seal.

10. The apparatus of claim 1, wherein both of said first and second members comprise said compartment.

11. The apparatus of claim 10, wherein said formulation is distributed evenly between each of said compartments.

12. The apparatus of claim 10, wherein each of said compartments comprises said at least one emergence aperture.

13. The apparatus of claim 1, wherein only one of said first and second members comprises said compartment.

14. The apparatus of claim 13, wherein one of said first and second members comprises said compartment and the other of said members weighs substantially the same as said member comprising said compartment when said compartment comprises said formulation so as to act as a counterbalance to said member comprising said compartment.

15. The apparatus of claim 1, wherein said beneficial insects or mites are predator insects or mites.

16. The apparatus of claim 15, wherein said predator insects or mites are *Amblyseius cucumeris, Frankliniella occidentalis*, or *Thrips tabaci*.

17. The apparatus of claim 15, wherein said formulation further comprises a predator food.

18. The apparatus of claim 17, wherein said predator food is viable grain or prey insects or mites.

19. The apparatus of claim 18 wherein said prey is *Tyrophagus* spp., *Acarus siro*, or combinations thereof.

20. The apparatus of claim 19, wherein said prey is *Tyrophagus putrescentiae, Tyrophagus tropicus*, or combinations thereof.

21. The apparatus of claim 19 wherein said formulation further comprises prey food.

22. The apparatus of claim 21, wherein said prey food is steamed bran or a 3:1 mix of yeast and wheat germ.

23. The apparatus of claim 20, wherein said formulation comprises *Amblyseius cucumeris* and *Tyrophagus putrescentiae* in a ratio of approximately 1:10.

24. The apparatus of claim 1, wherein said at least one emergence aperture has a diameter of between about 0.5 mm and about 5.0 mm.

25. The apparatus of claim 1, wherein said at least one emergence aperture is positioned in a region of said inner walls proximate to said hinge section.

26. The apparatus of claim 1, wherein said cropping environment is a sheltered cropping environment.

27. An apparatus for providing beneficial insects or mites to a cropping environment, comprising:
   (a) at least two strips of film material of approximately equal dimensions bonded together at the edges of said at least two strips, said strips having a long axis and a short axis;
   (b) at least one compartment defined by said bonded edges and a bond positioned parallel to said short axis of said strips, said compartment containing a formulation therein comprising beneficial insects or mites;
   (c) at least one emergence aperture in at least one of said strips, said emergence aperture positioned to provide passage to said beneficial insects or mites from said compartment to said cropping environment; and
   (d) a hinge section positioned approximately midway along and perpendicular to said long axis, wherein said hinge section permits folding of said strips upon themselves such that said apparatus is provided with an inverted V- or U-type conformation, wherein said at least one emergence aperture is located on the inside of said conformation.

28. The apparatus of claim 27, wherein said film material is water resistant and air permeable.

29. The apparatus of claim 28, wherein said film material is selected from the group consisting of paper, thermoplastic material, polythene-coated paper, polythene-coated fabric, and porous PTFE.

30. The apparatus of claim 29, wherein said film material comprises polythene-coated paper and the polythene has a density of between 5 and 100 $g/m^2$.

31. The apparatus of claim 29, wherein said film material is a paper selected from the group consisting of machine glazed bleached kraft paper, grid lacquer paper, and medical paper.

32. The apparatus of claim 27, wherein said bonded edges are substantially seamless seals effectively preventing water from collecting on said bonded edges.

33. The apparatus of claim 27, wherein said apparatus comprises two compartments oriented on opposing sides of said hinge section.

34. The apparatus of claim 33, wherein said formulation is distributed evenly between each of said compartments.

35. The apparatus of claim 33, wherein each of said compartments comprises said at least one emergence aperture.

36. The apparatus of claim 27, wherein said beneficial insects or mites are predator insects or mites.

37. The apparatus of claim 36, wherein said predator insects or mites are *Amblyseius cucumeris, Frankliniella occidentalis*, or *Thrips tabaci*.

38. The apparatus of claim 36, wherein said formulation further comprises a predator food.

39. The apparatus of claim 38, wherein said predator food is viable grain or prey insects or mites.

40. The apparatus of claim 39 wherein said prey is *Tyrophagus* sp., *Acarus siro*, or combinations thereof.

41. The apparatus of claim 40, wherein said prey is *Tyrophagus putrescentiae, Tyrophagus tropicus*, or combinations thereof.

42. The apparatus of claim 40 wherein said formulation further comprises prey food.

43. The apparatus of claim 42, wherein said prey food is steamed bran or a 3:1 mix of yeast and wheat germ.

44. The apparatus of claim 41, wherein said formulation comprises *Amblyseius cucumeris* and *Tyrophagus putrescentiae* in a ratio of approximately 1:10.

45. The apparatus of claim 27, wherein said at least one emergence aperture has a diameter of between about 0.5 mm and about 5.0 mm.

46. The apparatus of claim 27, wherein said cropping environment is a sheltered cropping environment.

47. The apparatus of claim 27, wherein said hinge section forms a hook from which to hang said apparatus.

48. An apparatus for providing beneficial insects or mites to a cropping environment, comprising:
(a) at least one strip of film material folded upon itself wherein the edges are bonded together, said folded strip having a long axis and a short axis;
(b) at least one compartment defined by said bonded edges and a bond positioned parallel to said short axis of said folded strip, said compartment containing a formulation therein comprising beneficial insects or mites;
(c) at least one emergence aperture in said strip, said emergence aperture positioned to provide passage to said beneficial insects or mites from said compartment to said cropping environment; and
(d) a hinge section positioned approximately midway along and perpendicular to said long axis, wherein said hinge section permits folding of said folded strip upon itself such that said apparatus is provided with an inverted V- or U-type conformation, wherein said at least one emergence aperture is located on the inside of said conformation.

49. The apparatus of claim 48, wherein said film material is water resistant and air permeable.

50. The apparatus of claim 49, wherein said film material is selected from the group consisting of paper, thermoplastic material, polythene-coated paper, polythene-coated fabric, and porous PTFE.

51. The apparatus of claim 50, wherein said film material comprises polythene-coated paper and the polythene has a density of between 5 and 100 g/m$^2$.

52. The apparatus of claim 49, wherein said film material is a paper selected from the group consisting of machine glazed bleached kraft paper, grid lacquer paper, and medical paper.

53. The apparatus of claim 48, wherein said bonded edges are substantially seamless seals effectively preventing water from collecting on said bonded edges.

54. The apparatus of claim 48, wherein said apparatus comprises two compartments oriented on opposing sides of said hinge section.

55. The apparatus of claim 54, wherein said formulation is distributed evenly between each of said compartments.

56. The apparatus of claim 54, wherein each of said compartments comprises said at least one emergence aperture.

57. The apparatus of claim 48, wherein said beneficial insects or mites are predator insects or mites.

58. The apparatus of claim 57, wherein said predator insects or mites are *Amblyseius cucumeris, Frankliniella occidentalis*, or *Thrips tabaci*.

59. The apparatus of claim 57, wherein said formulation further comprises a predator food.

60. The apparatus of claim 59, wherein said predator food is viable grain or prey insects or mites.

61. The apparatus of claim 60 wherein said prey is *Tyrophagus* sp., *Acarus siro*, or combinations thereof.

62. The apparatus of claim 61, wherein said prey is *Tyrophagus putrescentiae, Tyrophagus tropicus*, or combinations thereof.

63. The apparatus of claim 61 wherein said formulation further comprises prey food.

64. The apparatus of claim 63, wherein said prey food is steamed bran or a 3:1 mix of yeast and wheat germ.

65. The apparatus of claim 61, wherein said formulation comprises *Amblyseius cucumeris* and *Tyrophagus putrescentiae* in a ratio of approximately 1:10.

66. The apparatus of claim 48, wherein said at least one emergence aperture has a diameter of between about 0.5 mm and about 5.0 mm.

67. The apparatus of claim 48, wherein said cropping environment is a sheltered cropping environment.

68. The apparatus of claim 48, wherein said hinge section forms a hook from which to hang said apparatus.

* * * * *